United States Patent
Stutz et al.

(10) Patent No.: US 6,683,206 B2
(45) Date of Patent: Jan. 27, 2004

(54) PREPARATION OF (R -2-ALKYL-3-PHENYLPROPIONIC ACIDS

(75) Inventors: Stefan Stutz, Basel (CH); Peter Herold, Basel (CH); Felix Spindler, Starrkirch-Wil (CH); Walter Weissensteiner, Mödling (AT); Thomas Sturm, Vienna (AT)

(73) Assignee: Speedel Pharma AG, Basel (CH)

( * ) Notice: Subject to any disclaimer, the term of this patent is extended or adjusted under 35 U.S.C. 154(b) by 0 days.

(21) Appl. No.: 10/312,855

(22) PCT Filed: Jun. 26, 2001

(86) PCT No.: PCT/CH01/00397

§ 371 (c)(1),
(2), (4) Date: Jan. 2, 2003

(87) PCT Pub. No.: WO02/02500

PCT Pub. Date: Jan. 10, 2002

(65) Prior Publication Data

US 2003/0139625 A1 Jul. 24, 2003

(30) Foreign Application Priority Data

Jul. 3, 2000 (CH) ............................................. 1317/00

(51) Int. Cl.[7] ........................ C07C 63/64; C07C 229/00
(52) U.S. Cl. ...................... 562/465; 562/450; 502/162; 556/21
(58) Field of Search .............................. 562/465, 450; 502/162; 556/21

(56) References Cited

U.S. PATENT DOCUMENTS 5,426,216 A * 6/1995 Genet et al. ................. 562/450

OTHER PUBLICATIONS

Miyano et al, Bull. Chem. Jpn, vol. 57, (1984), pp. 2171–2176.*
Yamada et al, J. Chem. Soc., Perkins Trans. 1, (1990), 1869–1873.*
Zhang et al, Synlett, (1994), pp. 501–503.*
Miyano, Sotaro et al.: "Axially dissymmetric bis(aminophosphine)s derived from 2, 2'-diamino-1, 1'-binaphthyl. Synthesis and application to rhodium (I)-catalyzed asymmetric hydrogenations" Bull. Chem. Soc. Jpn. (1984), 57(8), 2171–6, XP002183784.
Appleton, Trevor D. et al.: "Rhodium (I) complexes of ferrocenylphosphines as efficient asymmetric catalysts. The structure of Fe(.eta, 5–C5H3(P(CMe3)2-1,3)(.eta.5–C5H3(CHMeNMe2)P(CMe3)2-1,2)" J. Organomet. Chem. (1985), 279 (1–2), 5–2', XP002183785.
Kawano, Hiroyuki et al.: "Ruthenium (II)–binap complex-catalyzed asymmetric hydrogenation of unsaturated dicarboxylic acids" Tetrahedron Lett. (1987), 28 (17), 1905–8, XP002183786 p. 1908.

Zhang, Xiaoyong et al.: "Highly enantioselective hydrogenation of .alpha., .beta.–unsaturated carboxylic acid catalyzed by H8–Binap–Ru(II) complexes" Synlett (1994), (7), 501–3, XP002183787.

Uemura, Toshitsugi et al.: "Highly Efficient Enantioselective Synthesis of Optically Active Carboxylic Acids by Ru(OCOCH3)2'(S)–H8–BINAP!" J. Org. Chem. (1996), 61(16), 5510–5516, XP002183788.

Shao, Liming et al.: "Asymmetric synthesis of (R)– and (S)-4(substituted benzyl)dihydrofuran–2(3H)–ones: an application of the ruthenium –2, 2'-bis(diphenylphosphino)–1, 1'-binaphthyl complex-catalyzed asymmetric hyrogenation of alkylidenesuccinic acids" J. Chem. Soc., Perkin Trans. 1 (1990), (5), 1441–5, XP002183789.

Yamada, Issaku et al.: "Asymmetric hydrogenation of acrylic acid derivatives by novel chiral rhodium–phosphinediamine complex catalysts by selective ligation between two amino units of the ligand and electrostatic interaction" J. Chem. Soc., Perkin Trans. 1 (1990), 1869–73, XP002183790.

Wei Y. et al.: "Aldol addition reaction of a lithium ester enolate in the solid state" Tetrahedron Letters, Elsevier Science Publishers, Amsterdam, NL, vol. 32, No. 12, Mar. 18, 1991, pp. 1535–1538, XP002175158.

(List continued on next page.)

*Primary Examiner*—Alan L. Rotman
*Assistant Examiner*—Hector M Reyes
(74) *Attorney, Agent, or Firm*—Wenderoth, Lind & Ponack, L.L.P.

(57) ABSTRACT

Compounds of formula (I), wherein $R_1$ and $R_2$ are, independently of one another, H, $C_1-C_6$alkyl, $C_1-C_6$halogenalkyl, $C_1-C_6$alkoxy, $C_1-C_6$alkoxy-$C_1-C_6$alkyl, or $C_1-C_6$alkoxy-$C_1$-$C_6$alkyloxy, and $R_3$ is $C_1-C_6$alkyl, are obtainable in high yields by stereoselective addition of $R_3$-substituted propionic acid esters to $R_1$- and $R_2$-substituted benzaldehydes of formula R—CHO to form corresponding 3-R-3-hydroxy-2-$R_3$-propionic acid esters, conversion of the OH group to a leaving group, subsequent regioselective elimination to form 3-R-2-$R_3$-propenic acid esters, and their hydrolysis to form corresponding propenic carboxylic acids and their enantioselective hydrogenation, wherein R is (a).

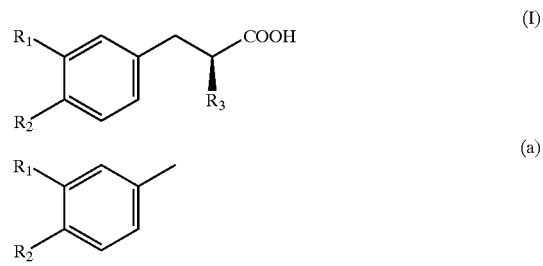

19 Claims, No Drawings

OTHER PUBLICATIONS

Bartoli, G. et al.: "An efficient procedure for the diastereoselective dehydration of beta–hydroxy carbonyl compounds by CeCl3,7H20/NaI system" Organic Letters, ACS, Washington, DC, US, vol. 2, No. 13, Jun. 1, 2000, pp. 1791–1793, XP002175161.

Yamada, T. et al.: "A preparative method of DL–threo–3–isopropylmalic acid and DL–threo–'2–2H!–3–isopropylmalic acid" Chemistry Letters, Chemical Society of Japan. Tokyo, JP, No. 9, Sep. 1987, pp. 1745–1748, XP002175183.

Jerry March: "Advanced organic chemistry, third edition" 1985, Wiley–Interscience, New York XP002183791.

* cited by examiner

PREPARATION OF (R -2-ALKYL-3-PHENYLPROPIONIC ACIDS

The invention relates to a stereoselective process for the preparation of (R)-2-alkyl-3-phenyl-propionic acids and intermediate products obtained in the process steps.

In EP-A-0 678 503, δ-amino-γ-hydroxy-ω-aryl-alkanecarboxamides are described which exhibit renin-inhibiting properties and could be used as antihypertensive agents in pharmaceutical preparations. The manufacturing processes described are unsatisfactory in terms of the number of process steps and yields and are not suitable for an industrial process. A disadvantage of these processes is also that the total yields of pure diastereomers that are obtainable are too small.

In a new process, one starts from 2,7-dialkyl-8-aryl-4-octenoyl amides, whose double bond is simultaneously halogenated in the 5-position and hydroxylated in the 4-position under lactonization, then the halogen is substituted by azide, the lactone amidated and the azide then transferred to the amine group. The desired alkanecarboxamides are obtained with the new process both in high total yields and in a high degree of purity, and selectively pure diastereomers can be prepared. The halolactonization of process step a), the azidation of process step b), and the azide reduction of process step d) are described by P. Herold in the Journal of Organic Chemistry, Vol. 54 (1989), pages 1178–1185.

The 2,7-dialkyl-8-aryl-4-octenoyl amides may correspond for example to formula A,

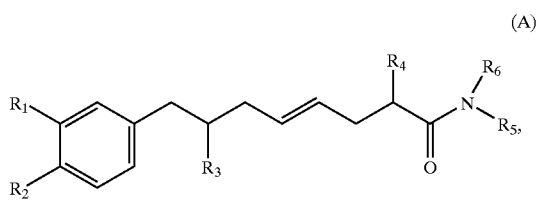

and especially to formula A1

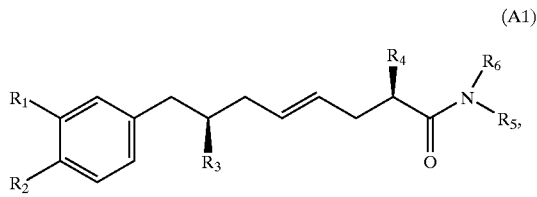

wherein $R_1$ and $R_2$ are, independently of one another, H, $C_1$–$C_6$alkyl, $C_1$–$C_6$halogenalkyl, $C_1$–$C_6$alkoxy, $C_1$–$C_6$alkoxy-$C_1$–$C_6$alkyl, or $C_1$–$C_6$alkoxy-$C_1$–$C_6$alkyloxy, $R_3$ is $C_1$–$C_6$alkyl, $R_4$ is $C_1$–$C_6$alkyl, $R_6$ is $C_1$–$C_6$alkyl, $R_5$ is $C_1$–$C_6$alkyl or $C_1$–$C_6$alkoxy, or $R_5$ and $R_6$ together are tetramethylene, pentamethylene, 3-oxa-1,5-pentylene or —$CH_2CH_2O$—$C(O)$— substituted if necessary with $C_1$–$C_4$alkyl, phenyl or benzyl.

The compounds of formulae A and A1 are obtainable by reacting a compound of formula B

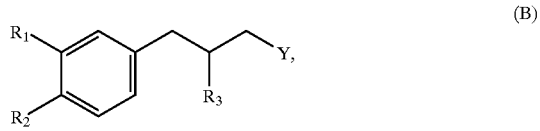

as racemate or enantiomer, with a compound of formula C, as racemate or enantiomer,

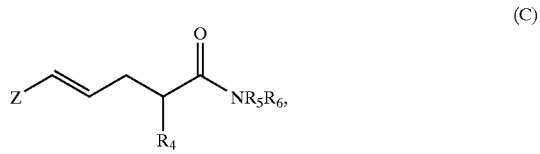

wherein $R_1$ to $R_4$, $R_5$ and $R_6$ are as defined above, Y is Cl, Br or I and Z is Cl, Br or I, in the presence of an alkali metal or alkaline earth metal. Y and Z are preferably Br and especially Cl.

The compounds of formula B are known from EP-A-0 678 503. The compounds of formula C may be prepared from amidation of the corresponding carbonic esters, amides, or halides. The formation of carboxamides from carbonic esters and amines in the presence of trialkyl aluminium or dialkyl aluminium halide, for example using trimethyl aluminium or dimethyl aluminium chloride, is described by S. M. Weinreb in Org. Synthesis, VI, page 49 (1988). The carbonic esters are obtainable by the reaction of trans-1,3-dihalogenpropene (for example, trans-1,3-dichlorepropene) with corresponding carbonic esters in the presence of strong bases, for example alkali metal amides.

A satisfactory solution for the stereoselective preparation of compounds of formula B has not yet been found, especially with regard to an industrial process. Surprisingly it has now been found that 2-alkyl-3-phenylpropionic acids can be stereoselectively prepared with high yields in only three process steps. When suitably substituted benzaldehydes are condensed with carbonic esters to form 2-alkyl-3-hydroxy-3-phenylpropionic acid esters, the desired diastereomers are obtainable in surprisingly high yields mostly as crystalline compounds which can be readily isolated. After conversion of the hydroxy group to a leaving group, 2-alkylcinnamic acid esters are then formed by elimination with strong bases with surprisingly high regioselectivity. The carboxylic acids obtained after saponification can in turn be surprisingly hydrogenated in the presence of homogeneous, asymmetric hydrogenation catalysts to form practically enantiomer-pure 2-alkyl-3-phenylpropionic acids. These acids can then be reduced in a manner known per se to form enantiomer-pure alcohols, from which the compounds of formula B are obtainable by halogenation.

The object of the invention is a process for the preparation of compounds of formula I,

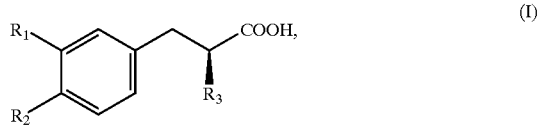

wherein $R_1$ and $R_2$ are, independently of one another, H, $C_1$–$C_6$alkyl, $C_1$–$C_6$halogenalkyl, $C_1$–$C_6$alkoxy, $C_1$–$C_6$alkoxy-$C_1$–$C_6$alkyl, or $C_1$–$C_6$alkoxy-$C_1$–$C_6$alkyloxy, and $R_3$ is $C_1$–$C_6$alkyl, comprising (a) the reaction of a compound of formula II

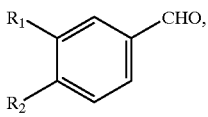

wherein $R_1$ and $R_2$ are as defined above, with a compound of formula III,

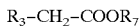

wherein $R_3$ is as defined above, to form a compound of IV,

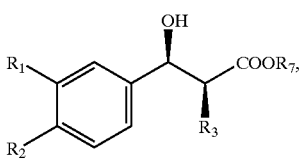

wherein $R_7$ is $C_1C_{12}$alkyl, $C_3$–$C_8$cycloalkyl, phenyl or benzyl, (b) the isolation of the crystalline compound of formula IV, the conversion of the OH group to a leaving group, and the reaction of a compound containing a leaving group in the presence of a strong base to form a compound of formula V,

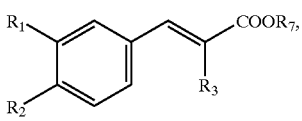

(c) the hydrolysis of carbonic esters of formula V to form the carboxylic acid of formula VI,

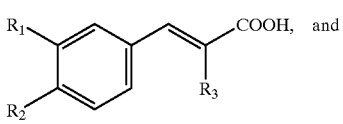

(d) the hydrogenation of the carboxylic acid of formula VI in the presence of hydrogen and catalytic quantities of a metal complex as asymmetric hydrogenation catalyst, comprising metals from the group of ruthenium, rhodium and iridium, to which the chiral bidentate ligands are bonded, to form a compound of formula I.

$R_1$ and $R_2$ may be a linear or branched alkyl and preferably comprise 1 to 4 C atoms. Examples are methyl, ethyl, n- and i-propyl, n-, i- and t-butyl, pentyl and hexyl.

$R_1$ and $R_2$ may be a linear or branched halogenalkyl and preferably comprise 1 to 4 C atoms, 1 or 2 C atoms being especially preferred. Examples are fluoromethyl, difluoromethyl, trifluoromethyl, chloromethyl, dichloromethyl, trichloromethyl, 2-chloroethyl and 2,2,2-trifluoroethyl.

$R_1$ and $R_2$ may be a linear or branched alkoxy and preferably comprise 1 to 4 C atoms. Examples are methoxy, ethoxy, n- and i-propyloxy, n-, i- and t-butyloxy, pentyloxy and hexyloxy.

$R_1$ and $R_2$ may be a linear or branched alkoxyalkyl. The alkoxy group preferably comprises 1 to 4 and especially 1 or 2 C atoms, and the alkyl group preferably comprises 1 to 4 C atoms. Examples are methoxymethyl, 1-methoxyeth-2-yl, 1-methoxyprop-3-yl, 1-methoxybut-4-yl, methoxypentyl, methoxyhexyl, ethoxymethyl, 1-ethoxyeth-2-yl, 1-ethoxyprop-3-yl, 1-ethoxybut-4-yl, ethoxypentyl, ethoxyhexyl, propyloxymethyl, butyloxymethyl, 1-propyloxyeth-2-yl and 1-butyloxyeth-2-yl.

$R_1$ and $R_2$ may be linear or branched $C_1$–$C_6$alkoxy-$C_1$–$C_6$alkyloxy. The alkoxy group preferably comprises 1 to 4 and especially 1 or 2 C atoms, and the alkyloxy group preferably comprises 1 to 4 C atoms. Examples are methoxymethyloxy, 1-methoxyeth-2-yloxy, 1-methoxyprop-3-yloxy, 1-methoxybut-4-yloxy, methoxypentyloxy, methoxyhexyloxy, ethoxymethyloxy, 1-ethoxyeth-2-yloxy, 1-ethoxyprop-3-yloxy, 1-ethoxybut-4-yloxy, ethoxypentyloxy, ethoxyhexyloxy, propyloxymethyloxy, butyloxymethyloxy, 1-propyloxyeth-2-yloxy and 1-butyloxyeth-2-yloxy.

In a preferred embodiment, $R_1$ is methoxy-$C_1$–$C_4$alkyloxy or ethoxy-$C_1$–$C_4$alkyloxy, and $R_2$ is preferably methoxy or ethoxy. Quite especially preferred are compounds of formula I, wherein $R_1$ is 1-methoxyprop-3-yloxy and $R_2$ is methoxy.

$R_3$ may be a linear or branched alkyl and preferably comprise 1 to 4 C atoms. Examples are methyl, ethyl, n- and i-propyl, n-, i- and t-butyl, pentyl and hexyl. In a preferred embodiment, $R_3$ in compounds of formula I is isopropyl.

Especially preferred are compounds of formula I wherein $R_1$ is ethoxy-n-propoxy, $R_2$ is methoxy and $R_3$ is isopropyl.

$R_7$ is preferably $C_1$–$C_6$alkyl, $C_1$–$C_4$alkyl being especially preferred; some examples are methyl, ethyl, n-propyl and n-butyl.

The starting compounds of formulae II and III used in process step a) are known or can be prepared in a manner similar to known processes. Compounds of formula II are described in EP-A 0 678 503. The reaction is advantageously carried out at low temperatures, for example 0–40° C., in the presence of at least equivalent quantities of strong bases. The reaction is further expediently carried out in a solvent, ethers such as diethyl ether, tetrahydrofuran and dioxane being especially suitable. Suitable strong bases are in particular alkali metal alcoholates and secondary amides, such as lithium diisopropylamide.

The desired diastereomer of formula IV is surprisingly formed up to about 75%. The compounds of formula IV are surprisingly crystalline and can therefore be readily isolated without any substantial losses by means of extraction and crystallization.

The conversion of the OH group to a leaving group in reaction step b) is known per se. Reaction with carboxylic acids or sulfonic acids, or their anhydrides (acylation), is especially suitable. Some examples of carboxylic acids are formic acid, acetic acid, propionic acid, benzoic acid, benzenesulfonic acid, toluenesulfonic acid, methylsulfonic acid and trifluoromethylsulfonic acid. The use of acetic acid anhydride has proved especially successful. The elimination is expediently carried out in the presence of strong bases, alkali metal alcoholates such as potassium t-butylate being especially suitable. The presence of solvents such as ethers is expedient. The reaction is advantageously carried out at low temperatures, for example 0–40° C. It is of advantage to conduct the elimination reaction directly in the reaction mixture for acylation. The elimination leads to the desired Z isomers with surprisingly high regioselectivity. These isomers are crystalline and can therefore be readily isolated without any substantial losses by means of extraction and crystallization. The yields are above 80%.

Hydrolysis of the ester of formula V to form the carboxylic acids of formula VI in process step c) is a generally known reaction. The hydrolysis may be carried out after isolation and purification of the compound of formula III. It is expedient to add water to the reaction mixture of process step b), to evaporate off the solvent and then to carry out alkaline or acidic hydrolysis. The carboxylic acids of formula VI are crystalline and can be readily isolated in yields of 80% or more.

The asymmetric hydrogenation in process step d) of α,β-unsaturated carboxylic acids with homogeneous, asymmetric hydrogenation catalysts is known per se and described for example by John M. Brown in E. Jacobsen, A. Pfaltz, H. Yamamoto (Eds.), Comprehensive Asymmetric Catalysis I to III, Springer Verlag, 1999, pages 121 to 182. Especially effective are ruthenium and rhodium catalysts. Chiral ditertiary diphosphines whose phosphine groups in the 1,2, 1,3 or 1,4 position are bonded to a $C_2$–$C_4$ carbon chain are often used as ligands. The skeletal structures of the chiral ditertiary diphosphines may be acyclic, monocyclic or polycyclic. The phosphine groups may be substituted with the same or with different, preferably the same, substituents selected from the group of $C_1$–$C_8$alkyl, $C_3$–$C_8$cycloalkyl, $C_6$–$C_{12}$aryl, and $C_6$–$C_{12}$aryl-$C_1$–$C_4$alkyl. Cycloalkyl and aryl may be unsubstituted or substituted with $C_1$–$C_4$alkyl, $C_1$–$C_4$alkoxy, $C_1$–$C_4$fluoroalkyl or $C$–$C_{12}$secondary amino. Suitable phosphine groups are also phosphanyl, preferably five-member phosphanyl, which if necessary is substituted in one or both α-positions with $C_1$–$C_4$alkyl or $C_1$–$C_4$alkoxy.

Some examples of chiral ditertiary diphosphines are (R"$_2$P is for example diphenylphosphino or dicyclohexylphosphino, substituted if necessary) 1,2-Di-R"$_2$P-propane, 2,3-Di-R"$_2$P-butane, 1,2-Di-R"$_2$P-norbornane or -norbornadiene, 1,2-Di-R"$_2$P-cyclopentane, 1,2-Di-R"$_2$P-N-methylpyrrolidine, 2,2"-Di-R"$_2$P-biphenyl or -binaphthyl, 2,2"-Di-R"$_2$P-6-methyl or -6,6'-dimethylbiphenyl, 2,2'-Di-R"$_2$P-6-methoxy or -6,6'-dimethoxy-biphenyl, and 1-(α-R"$_2$P-ethyl)-2-R"$_2$P-ferrocene.

Good optical yields are achieved using metal complexes of formula VII or VIIa,

[LMeYZ]  (VII),

[LMeY]$^+$E$^-$  (VIIa), wherein
Me is rhodium;
Y stands for two olefins or one diene;
Z is Cl, Br or I;
E$^-$ is the anion of an oxygen acid or a complex acid; and
L is a chiral ligand from the group of ditertiary diphosphines, in which the phosphine groups are bonded to a $C_2$–$C_4$ chain of the diphosphine backbone chain, and the diphosphine forms a five to seven-member ring together with the rhodium atom.

Where Y stands for two olefins, they may be $C_2$–$C_{12}$ olefins, $C_2$–$C_6$olefins being preferred and $C_2$–$C_4$olefins being especially preferred. Examples are propene, but-1-ene and especially ethylene. The diene may comprise 5 to 12 and preferably 5 to 8 C atoms and may be an acyclic, cyclic or polycyclic diene. The two olefin groups of the diene are preferably linked by one or two $CH_2$ groups. Examples are 1,3-pentadiene, cyclopentadiene, 1,5-hexadiene, 1,4-cyclohexadiene, 1,4- or 1,5-heptadiene, 1,4- or 1,5-cycloheptadiene, 1,4- or 1,5-octadiene, 1,4- or 1,5-cyclooctadiene and norbornadiene. Y represents preferably two ethylene or 1,5-hexadiene, 1,5-cyclooctadiene or norbornadiene.

In formula VII, Z is preferably Cl or Br. Examples of $E_1$ are $ClO_4^-$, $CF_3SO_3^-$, $CH_3SO_3^-$, $HSO_4^-$, $BF_4^-$, $B(phenyl)_4^-$, $PF_6^-$, $SbCl_6^-$, $ASF_6^-$ or $SbF_6^-$.

With known ligands for asymmetric catalysts, optical yields of up to about 80% ee can be achieved under optimized conditions. It was surprisingly found that new ligands with a ferrocenyl backbone are especially suitable for asymmetric hydrogenation of the compounds of formula VI. With these new ligands in the metal complexes of formulae VII and VIIa, optical yields of at least 95% ee can be achieved, which represents a substantial cost saving for manufacture on an industrial scale. In process step d), therefore, it is preferred to use metal complexes of formulae VII and VIIa which comprise ligands of formula VIII or VIIIa,

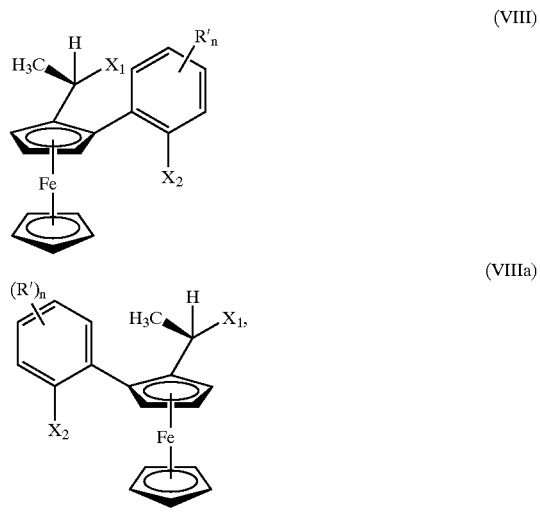

wherein
n is 0 or an integer from 1 to 4 and R' represents the same or different substituents selected from the $C_1$–$C_4$alkyl, —$CF_3$ and $C_1$–$C_4$alkoxy group; and
$X_1$ and $X_2$ are, independently of one another, secondary phosphino.

As an alkyl, R' may preferably comprise 1 to 2 C atoms. Linear alkyl is preferred. Examples of R' as an alkyl are methyl, ethyl, n- and i-propyl, n-, i- and t-butyl. Methyl and ethyl are preferred, and methyl is especially preferred.

As an alkoxy, R' may preferably comprise 1 to 2 C atoms. Linear alkoxy is preferred. Examples of R' as an alkoxyl are methoxy, ethoxy, n- and i-propoxy, n-, i- and t-butoxy. Methoxy and ethoxy are preferred and methoxy is especially preferred.

The $X_1$ and $X_2$ groups may be different or preferably the same and correspond to formula $PR_8R_9$, wherein $R_8$ and $R_9$ are the same or different and represent branched $C_3$–$C_8$alkyl, $C_3$–$C_8$cycloalkyl, or unsubstituted or phenyl substituted with one to three $C_1$–$C_4$alkyl, $C_1$–$C_4$-alkoxy, or —$CF_3$.

Special preference is for ligands of formulae VIII and VIIIa, wherein n is 0, and $X_1$ and $X_2$ are a $PR_8R_9$ group, wherein $R_8$ and $R_9$ in each case are cyclohexyl, phenyl or phenyl substituted with 1 or 2 methyl, methoxy or $CF_3$.

The new ligands are prepared by means of reactions that are known per se or analogous to known reactions, such as those described in U.S. Pat. No. 5,371,256, U.S. Pat. No. 5,446,844 and U.S. Pat. No. 5,583,241. Ligands with other phosphine groups may be prepared in a manner analogous to the method described in the example.

The metal complexes used as catalysts may be added as separately prepared isolated compounds, or also formed in situ before the reaction and then mixed with the substrate to be hydrogenated. It may be advantageous in the reaction using isolated metal complexes to add additional ligands, or in the in situ preparation to use surplus ligands. The surplus may for example be up to 10 moles and preferably 0.001 to 5 moles, based on the metal complexes used for the preparation.

Process step d) may be carried out at low or elevated temperatures, for example at temperatures from −20 to 150° C., preferably from −10 to 100° C., temperatures of 10 to 80° C. being especially preferred. The optical yields are generally better at low temperatures than at high temperatures.

The process according to the invention may be carried out at normal pressure or preferably under positive pressure. The pressure may for example range from $10^5$ to $2 \times 10^7$ Pa (Pascal).

Catalysts are preferably used in quantities from 0.0001 to 10 mol-% based on the compound to be hydrogenated, the range 0.001 to 10 mol-% being especially preferred and the range 0.01 to 5 mol-% being preferred in particular.

The preparation of catalysts as well as process step d) and the other process steps may be carried out in the absence or the presence of an inert solvent, wherein one solvent or a mixture of solvents may be used. Suitable solvents are, for example, aliphatic, cycloaliphatic and aromatic hydrocarbons (pentane, hexane, petroleum ether, cyclohexane, methylcyclohexane, benzene, toluene, xylene), aliphatic halogenated hydrocarbons (dichloromethane, chloroform, di- and tetrachloroethane), nitrites (acetonitrile, propionitrile, benzonitrile), ethers (diethyl ether, dibutyl ether, t-butyl methyl ether, ethylene glycol dimethyl ether, ethylene glycol diethyl ether, diethylene glycol dimethyl ether, tetrahydrofuran, dioxane, diethylene glycol monomethyl or monoethyl ether), ketones (acetone, methyl isobutyl ketone), carbonic esters and lactones (ethyl or methyl acetate, valerolactone), N-substituted lactams (N-methylpyrrolidone), carboxamides (dimethylamide, dimethylformamide), acyclic ureas (dimethylimidazoline), and sulfoxides and sulfones (dimethyl sulfoxide, dimethyl sulfone, tetramethylene sulfoxide, tetramethylene sulfone) and alcohols (methanol, ethanol, propanol, butanol, ethylene glycol monomethyl ether, ethylene glycol monoethyl ether, diethylene glycol monomethyl ether) and water. The solvents may be used alone or in a combination of at least two solvents.

The reaction may be carried out in the presence of co-catalysts, for example quaternary ammonium halogenides (tetrabutylammonium iodide) and/or in the presence of protonic acids, for example mineral acids.

Using the regioselective and enantioselective process according to the invention, the intermediate products of formula (B) may be prepared via all process steps in yields of at least 50% by weight, based on the compounds of formula II. The high total yields make the process suitable for industrial use.

A further object of the invention relates to the compounds (intermediates) of formula IX,

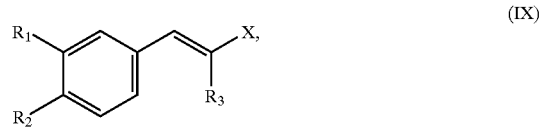

wherein $R_1$, $R_2$ and $R_3$ are as defined hereinbefore and X is the —COOH group.

The embodiments and preferences described hereinabove apply for $R_1$, $R_2$, and $R_3$.

The following examples explain the invention in more detail.

A) Preparation of the Ligands

EXAMPLE A1

Preparation of

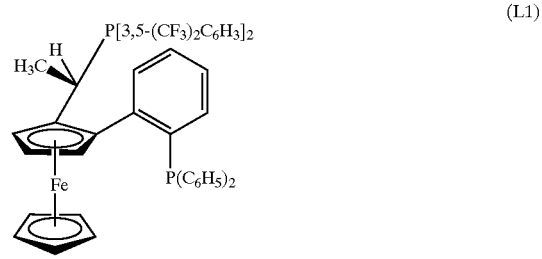

(L1)

a) Preparation of $(R_C,S_P)$-2-(2-bromophenyl)-1-[1-N,N-dimethylamino)ethyl]ferrocene, L2

At 0° C., 33 ml (43 mmol) of a 1.3 molar solution of s-butyl lithium in cyclohexane is added dropwise to a degassed solution of 10 g (38.9 mmol) (+)-(R)-1-N,N-dimethyl-aminoethyl ferrocene (L1) in 32 ml tetrahydrofuran (THF). After 30 minutes, still at 0° C., 44 ml of a 1 molar solution of $ZnCl_2$ in diethyl ether is added drop by drop. The reaction mixture is then stirred for one hour at room temperature. After the addition of 1.4 g (2 mmol) bis-diphenylphosphino-palladium(II) chloride and a solution of 22.64 g (80 mmol) 2-bromo-1-iodobenzene in 50 ml THF, the reaction mixture is heated for 3 days under reflux. The solvent is removed on a rotary evaporator, the residue taken up in $CH_2Cl_2$ and extracted with water. The aqueous phase is extracted 3 times with 30 ml $CH_2Cl_2$ and the combined organic phases are washed twice with 20 ml water. After drying over $MgSO_4$ and removal of the solvent in a vacuum, the residue is chromatographed on aluminium oxide 90. A mixture of petroleum ether, ether and triethylamine in a ratio of 60:1:3 is used as the mobile phase. The yield amounts to 4.65 g (11.3 mmol, 30%).

$^1$H-NMR: δ 1.61 (d, J=7.0 Hz, 3H), 1.75 (s, 6H), 3.54 (q, J=7.0 Hz, 1H), 4.13 (s, 5H, Cp), 4.23–4.25 (m, 1H, Cp), 4.32–4.34 (m, 1H, Cp), 4.59–4.61 (m, 1H, Cp), 7.07–7.11 (m, 1H, Ph), 7.30–7.35 (m, 1H, Ph), 7.51–7.53 (m, 1H, Ph), 7.85–7.87 (m, 1H, Ph).

$[\alpha]^{20}$ (nm): +75.9° (589), +61.4° (578), −45.4° (546) (c=1, $CHCl_3$)

b) Preparation of $(R_C,S_P)$-1-[1-(N,N-dimethylamino)ethyl]-2-(2-diphenylphosphinophenyl)-ferrocene, L3

At −40° C., 4.5 ml of a 1.3 molar solution of s-butyl lithium in cyclohexane is slowly added drop by drop to a degassed solution of 2 g (4.87 mmol) of L2 in 25 ml THF. After 40 minutes, the reaction mixture is allowed to warm up to room temperature, and then 1.1 ml (6.6 mmol) diphenylchloro-phosphine is added drop by drop. After 18 hours, 30 ml saturated NaHCO$_3$ solution is added. The organic phase is separated off and the aqueous phase is extracted twice with 20 ml CH$_2$Cl$_2$. The combined organic phases are washed twice with 20 ml water and dried over MgSO$_4$. After removal of the solvent in a vacuum and chromatography on silica gel 60 (petroleum ether/diethylamine=95:5) a yield of 2.15 g (4.16 mmol, 85.4%) of the product is obtained.

$^1$H-NMR: δ 1.64 (d, J=7.0 Hz, 3H), 1.86 (s, 6H), 3.72 (q, J=7.0 Hz, 1H), 4.04–4.06 (m, 1H, Cp), 4.08 (s, 5H, Cp), 4.22 (m, 1H, Cp), 4.25 (m, 1H, Cp), 6.93–6.98 (m, 2H, Ph), 6.99–7.02 (m, 1H, Ph), 7.15–7.20 (m, 4H, Ph), 7.31–7.40 (m, 6H, Ph), 7.94–7.98 (m, 1H, Ph).

$^{31}$P-NMR: δ −14.09.

[α]$^{20}$ (nm): −23.7° (589), −47.5° (578), −203.2° (546) (c=1, CHCl$_3$)

c) Preparation of $(R_C,S_P)$-1-[1-(N,N-dimethylamino) ethyl]-2-(2-diphenylphosphinylphenyl)-ferrocene, L4

To a solution of 1 g (1.93 mmol) L3 in 15 ml acetone, 0.8 ml 30% H$_2$O$_2$ is added dropwise. The solution is stirred for 45 minutes at room temperature, and then 20 ml saturated Na$_2$S$_2$O$_5$ solution is added. After extraction 3×25 ml CH$_2$Cl$_2$ the combined organic phases are washed with 2×20 ml water and dried over MgSO$_4$. The solvent is removed in a vacuum and the product purified by chromatography on aluminium oxide 90.

Non-polar impurities are removed by elution with a mixture of petroleum ether and ethyl acetate in a ratio of 80:20, and the product is then eluted with methanol. A yield of 990 mg (1.86 mmol, 96%) product is obtained.

$^1$H-NMR: δ 1.67 (d, J=7.0 Hz, 3H), 2.03 (s, 6H), 4.04 (s, 5H, Cp), 4.04 (q, J=7.0 Hz, 1H), 4.09–4.11 (m, 1H, Cp), 4.21–4.23 (m, 1H, Cp), 4.26 (m, 1H, Cp), 7.05–7.11 (m, 1H, Ph), 7.18–7.23 (m, 1H, Ph), 7.28–7.33 (m, 2H, Ph), 7.34–7.43 (m, 3H, Ph), 7.48–7.60 (m, 4H, Ph), 7.65–7.71 (m, 2H, Ph), 8.10–8.13 (m, 1H, Ph).

$^{31}$P-NMR: δ 31.67.

[α]$^{20}$ (nm): −160° (589), −200.6° (578), −449.4° (546) (c=0.5, CHCl$_3$)

d) Preparation of $(R_C,S_P)$-1-{1-[bis-(bis-3,5-trifluoromethylphenyl)phosphino]ethyl}-2-(2-diphenylphosphinylphenyl)ferrocene, L6

To a degassed solution of 1.25 g (2.35 mmol) L4 in 15 ml freshly distilled acetic acid, 1.6 g (3.5 mmol) bis-(3,5-trifluoromethylphenyl)phosphine is added. The reaction mixture is then agitated for 3 days at 100° C. The solvent is removed in a vacuum, the residue dissolved in CH$_2$Cl$_2$ and chromatographed on aluminium oxide 90. Non-polar impurities are removed by elution with hexane, and subsequent elution with a mixture of CH$_2$Cl$_2$ and methanol in a ratio of 99:1 yields 2.09 g (2.21 mmol, 88.9%) of product. Two diastereomers are formed in a ratio of 6:1 (determined by $^{31}$P-NMR), but these are not separated. The $^1$H-NMR data are those of the principal isomer.

$^1$H-NMR: δ 1.32 (dd, J$_1$=6.1 Hz, J$_2$=6.8 Hz, 3H), 3.47 (m, 1H, Cp), 3.79 (dq, J$_1$=2.8 Hz, J$_2$=7.1 Hz, 1H), 3.96 (t, J=2.8 Hz, Cp), 4.08 (s, 5H, Cp), 5.03 (m, 1H, Cp), 7.1–7.15 (m, 2H, Ph), 7.20–7.30 (m, 3H, Ph), 7.42–7.53 (m, 3H, Ph), 7.56–7.75 (m, 8H, Ph), 7.86 (s, 2H, Ph), 8.24–8.28 (m, 1H, Ph).

$^{31}$P-NMR: main component: δ 4.63, 30.29; secondary component: δ 4.77, 29.67.

e) Preparation of Title Compound $(R_C,S_P)$-1-{1-[bis-(bis-3,5-trifuoromethylphenyl)phosphino]-ethyl}-2-(2-diphenylphosphinophenyl)ferrocene, L1

To a degassed solution of 1.97 g (2.08 mmol) L6 in 20 ml THF, 9.2 ml polymethyl hydrosiloxane and 5.04 ml Ti(Oi-Propyl)$_4$ are added. The reaction mixture is heated under reflux for 18 hours, during which the solution turns a dark violet colour. Then 15 ml hexane is added and heated for a further 2 hours under reflux. The reaction mixture is applied to an aluminium oxide column without any further preparation, and the product is eluted with a mixture of petroleum ether, ethyl acetate and methanol in a ratio of 90:10:1. The yield amounts to 1.78 g (1.91 mmol, 91.8%). The two diastereomers are separated by chromatography on silica gel. A mixture of petroleum ether and CH$_2$Cl$_2$ in a ratio of 80:20 is used as the mobile phase.

$^1$H-NMR: δ 1.32 (dd, J$_1$=6.1 Hz, J$_2$=6.8 Hz, 3H), 3.29 (s, 1H, Cp), 3.66 (dq, J$_1$=J$_2$=7.1 Hz, 1H), 3.86 (m, 1H, Cp), 4.02 (t, J=2.5 Hz, 1H, Cp), 4.16 (s, 5H, Cp), 7.06–7.11 (m, 2H, Ph), 7.13–7.19 (m, 3H, Ph), 7.25–7.29 (m, 2H, Ph), 7.38–7.50 (m, 6H, Ph), 7.59 (d, J=4.0 Hz, 2H, Ph), 7.80 (s, 1H, Ph), 7.90 (s, 1H, Ph), 7.97 (d, J=6.1 Hz, 2H, Ph), 8.12–8.15 (m, 1H, Ph).

$^{31}$P-NMR: main component: δ −14.04 (d, J=23.5 Hz), 3.55 (d, J=23.5 Hz); secondary component: δ −15.19 (d, J=28.5 Hz), −5.16 (d, J=28.5 Hz).

[α]$_{20}$ (nm): −0.88 (589), −7.72 (578), −52.8 (546) (c=0.57, CHCl$_3$).

B) Preparation of (R)-3-[4'-CH$_3$O-3'-(CH$_3$O(CH$_2$)$_3$O)-phen-1-yl]-2-isopropylpropionic Acid

EXAMPLE B1

Preparation of

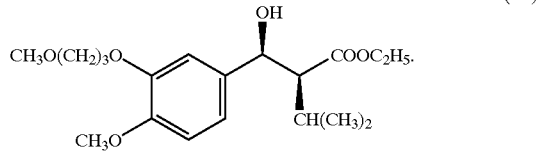

(B1)

A solution of 436 ml diisopropylamine and 2.6 l tetrahydrofuran is cooled to −20° C., and 1.234 l n-hexyl lithium (2.5 M in hexane) is added dropwise over a period of 15 minutes. A solution of 368 g ethyl isovalerate in 1.7 l tetrahydrofuran is added dropwise over a period of 15 minutes at −20° C. After a further 10 minutes, a solution of 584 g 4-methoxy-3-(3-methoxy-propoxy)benzaldehyde (EP 0 678 503) in 1.7 l tetrahydrofuran is added drop by drop and stirred for 40 minutes at −20° C. Then 2.15 l saturated aqueous ammonium chloride solution is added drop by drop and extracted with ethyl acetate (2×8 l). The organic phases are washed consecutively with 0.5 N hydrochloric acid (1×4.3 l), water (1×4.4 l) and brine (1×4.4 l). The combined organic phases are dried over sodium sulfate (1.6 kg), filtered and boiled down in a rotary evaporator. By means of crystallization from ethyl acetate (1 l) and hexane (11 l), title compound B1 is obtained from the residue as a white solid (656 g, 72%): $^1$H-NMR (400 MHz, DMSO-d$_6$, δ): 0.90–1.04 (m, 9H), 1.97 (m, 2H), 2.32 (m, 1H), 2.58 (m, 1H), 3.28 (s, 3H), 3.50 (m, 2H), 3.74 (s, 3H), 3.82 (q, 2H), 3.98 (m, 2H), 4.57 (m, 1H), 5.30 (d, 1H), 6.75–6.90 (m, 3H) ppm.

EXAMPLE B2

Preparation of

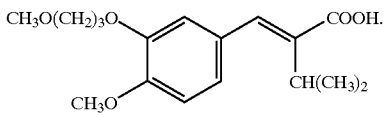
(B2)

A solution of 649 g (content: 98.3%) B1 and 11.0 g 4-dimethylaminopyridine in 3.2 l tetrahydrofuran is cooled to 0° C., 187.2 ml acetic acid anhydride is added dropwise and the reaction mixture then stirred for 1 hour. A solution of 606 g potassium t-butylate in 4.4 l tetrahydrofuran is added drop by drop over a period of 30 minutes at −2° C. to 0° C. and then stirred for 2 hours at 0° C. After the addition of 2 l water and distilling off 7.6 l tetrahydrofuran at 35° C., 6.5 l ethanol and 0.9 l 2N KOH are added to the aqueous residue. The mixture obtained is stirred for 20 hours under reflux. The reaction solution is cooled off and concentrated by evaporation. At 0° C., 7.2 l t-butyl methyl ether and 3 l 2N HCl are added to the residue. The organic phase is separated off and the aqueous phase extracted again with 7.2 l t-butyl methyl ether. The organic phases are then washed consecutively with 7.2 l water and 7.2 l brine. The combined organic phases are dried over magnesium sulfate (2 kg), filtered and concentrated in a rotary evaporator. By means of crystallization from diisopropyl ether (2.4 l) and hexane (2.4 l), 470 g of crude title compound is obtained from the residue. After recrystallization from diisopropyl ether (2 l) and Hexan (2 l), pure title compound B2 (454.3 g, 81.8%) is obtained: $^1$H-NMR (400 MHz, DMSO-d$_6$, δ): 1.22 (d, 6H), 1.97 (m, 2H), 3.14 (m, 1H), 3.28 (s, 3H), 3.50 (m, 2H), 3.82 (s, 3H), 4.02 (m, 2H), 6.90–7.05 (m, 3H), 7.42 (s, 1H), COOH (exchanged) ppm.

EXAMPLE B3

Preparation of

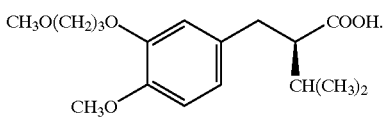
(B3)

In a flask with a magnetic stirrer, 5.83 mg (0.0156 mmol) [Rh(NBD)$_2$]BF$_4$ and 15.3 mg (0.0164 mmol) L1 are placed under an atmosphere of argon through repeated evacuation and purging with argon. Then 20 ml degassed methanol is added and stirred for 15 minutes, before 24 g (0.078 mol) B2 and 140 ml degassed methanol are introduced into a 250 ml flask fitted with a side stopcock and flushed with argon. With gentle heating, agitation is continued until a homogeneous solution is formed. The solution is forced under pressure via a steel capillary tube into a 300 ml steel autoclave under cover of argon. In 3 purge cycles (argon 20 bar/hydrogen 20 bar) the hydrogen pressure is eventually increased to 50 bar. Hydrogenation is started by switching on the stirrer and carried out at room temperature. The reaction takes place via hydrogen consumption (fall of pressure in the reservoir of hydrogen). After a reaction time of 8 hours, a full conversion is measured by HPLC (method 1). The reaction mixture is concentrated by evaporation and crude title compound B3 obtained as a slightly yellowish oil (24 g, quantitative): HPLC (method 2) optical yield >95% R-Isomer; $^1$H-NMR (400 MHz, CDCl$_3$, δ): 1.03 (m, 6H), 1.95 (m, 1H), 2.07 (m, 2H), 2.48 (m, 1H), 2.81 (m, 2H), 3.40 (s, 3H), 3.60 (m, 2H), 3.85 (s, 3H), 4.10 (m, 2H), 6.70–6.80 (m, 3H) ppm.

EXAMPLE B4

Preparation of

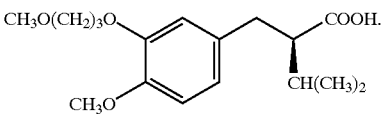
(B3)

In a flask with a magnetic stirrer, 1.50 mg (0.0024 mmol) [Rh(NBD) (OOCCF$_3$]$_2$ and 4.75 mg (0.0051 mmol) L1 are placed under an atmosphere of argon through repeated evacuation and purging with argon. Then 5 ml degassed methanol is added and stirred for 15 minutes, before 3.0 g (9.73 mmol) B2 and 15 ml degassed methanol are introduced into a 50 ml flask fitted with a side stopcock and flushed with argon. With gentle heating, agitation is continued until a homogeneous solution is formed. The solution is forced under pressure via a steel capillary tube into a 50 ml steel autoclave under cover of argon. In 3 purge cycles (argon 20 bar/hydrogen 20 bar) the hydrogen pressure is eventually increased to 20 bar. Hydrogenation is started by switching on the stirrer and carried out at room temperature. The reaction takes place via hydrogen consumption (fall of pressure in the reservoir of hydrogen). After a reaction time of 20 hours, a full conversion is measured. The optical yield amounts to >95% (R)-compound.

EXAMPLE B5

Preparation of

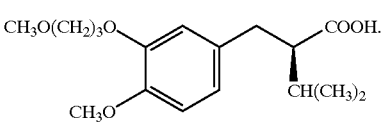
(B3)

In a flask with a magnetic stirrer, 1.50 mg (0.0024 mmol) [Rh(NBD) (OOCCF$_3$]$_2$ and 4.75 mg (0.0051 mmol) L1 are placed under an atmosphere of argon through repeated evacuation and purging with argon. Then 5 ml degassed toluene is added and stirred for 15 minutes, before 150 mg (0.486 mmol) B2 and 15 ml degassed toluene are introduced into a 50 ml flask fitted with a side stopcock and flushed with argon. With gentle heating, agitation is continued until a homogeneous solution is formed. The solution is forced under pressure via a steel capillary tube into a 50 ml steel autoclave under cover of argon. In 3 purge cycles (argon 20 bar/hydrogen 20 bar) the hydrogen pressure is eventually increased to 100 bar. Hydrogenation is started by switching on the stirrer and carried out at room temperature. The reaction takes place via hydrogen consumption (fall of pressure in the reservoir of hydrogen). After a reaction time of 72 hours, a full conversion is measured. The optical yield amounts to 95% (R)-compound.

EXAMPLE B6

Preparation of

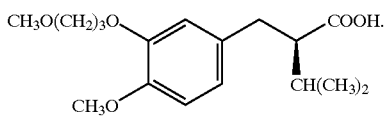 (B3)

The procedure is analogous to that described under Example B5. For preparation of the catalyst, 1.5 mg (0.004 mmol) [Rh(NBD)Cl]$_2$ and 3.86 mg (0.004 mmol) (2S,4S)-N-(t-butyl-oxycarbonyl)-4-(dicyclohexylphosphino)-2-(diphenylphosphino-methyl)pyrrolidine are used. 0.205 g (0.65 mmol) of educt B2 is hydrogenated in 10 ml toluene. After 20 hours at 60 bar hydrogen and 50° C., the reaction is stopped and the conversion and enantiomeric purity are determined. The conversion amounts to 98.9% and the optical yield is 80% ee.

EXAMPLE B7

Preparation of

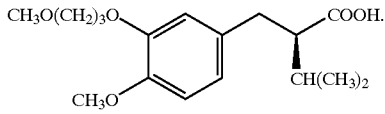 (B3)

The procedure is analogous to that described under Example B6, and 2.2 mg (0.01 mmol) [Rh(NBD)Cl]$_2$ and 9.6 mg (0.01 mmol) (R)-1,1'-(di-3,4,5-methoxyphenylphosphino)-6,6'-di-methoxybiphenyl are used for the preparation of the catalyst. 0.304 g (0.99 mmol) of educt B2 is hydrogenated in 10 ml toluene. After a reaction time of 18 hours at 60 bar hydrogen and 50° C., the conversion amounts to 93.5% and the optical yield is 73.5% ee.

EXAMPLE B8

Preparation of

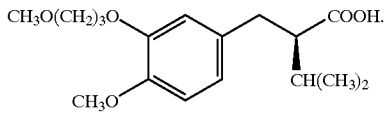 (B3)

The procedure is analogous to that described under Example B6, and 3.0 mg (0.01 mmol) [Rh(NBD)Cl]$_2$ and 6.19 mg (0.01 mmol) (R)-(S)-1-{1-[bis-(bis-t-butylphenyl)phosphino]ethyl}-2-(diphenylphosphino)ferrocene are used for the preparation of the catalyst. 0.227 g (0.74 mmol) of educt B2 is hydrogenated in 10 ml toluene. After a reaction time of 90 hours at 60 bar hydrogen and 30° C., the conversion amounts to 98.6% and the optical yield is 49% ee.

EXAMPLE B9

Preparation of

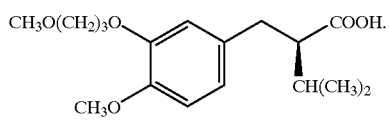 (B3)

In a 50 l steel autoclave are placed 25 l of methanol under an atmosphere of argon through repeated evacuation and purging with argon. Then 12.00 kg B2 are added under argon. The suspension is heated under argon (2 bar) to 50° C., cooled to 35° C. and degassed. 2.634 g (6.486 mmol) [Rh(COD)$_2$]BF$_4$ and 6.337 g (6.810 mmol) L1 are placed in a flask with magnetic stirrer under an atmosphere of argon through repeated evacuation and purging with argon. Then 700 ml degassed methanol are added and stirred for 45 minutes. This catalyst solution is forced under argon atmosphere through a steel capillary in the autoclave. In 3 purge cycles (argon 20 bar/hydrogen 20 bar) the hydrogen pressure is increased to 50 bar. The hydrogenation is started by switching on the stirrer and carried out at 350 C. The reaction is monitored via hydrogen consumption (decrease of pressure in the reservoir of hydrogen). After a reaction time of 21 hours (15 hours take-up of hydrogen) a full conversion is measured according to HPLC (methode 1). The reaction mixture is concentrated by evaporation and crude title compound B3 obtained as slightly yellowish oil (12.08 kg, quantitative): HPLC (Methode 2) optical yield >95% R-Isomer.

Determination of Conversion and Optical Yield:

For the HPLC analysis, B1 and B2 are derivatized (preparation of the respective methyl esters): a sample of the residue in diethyl ether is mixed with excess diazo methane in diethyl ether. The solvent is then evaporated off, and the residue obtained is the corresponding methyl ester.

Method 1 (determination of conversion): column HP Hypersil BDS-C 18 125×4 mm; acetonitrile and water 5% to 100%; 40 minutes flow: 0.8 ml.

Method 2 (determination of optical yield): column: Daicel OJ-R 0.45×15 cm; solvent 30% acetonitrile and 70% water.

What is claimed is:

1. A process for the preparation of compounds of formula I,

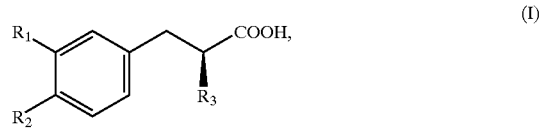 (I)

wherein R$_1$ and R$_2$ are, independently of one another, H, C$_1$–C$_6$alkyl, C$_1$–C$_6$halogenalkyl, C$_1$–C$_6$alkoxy, $C_1$–$C_6$alkoxy-$C_1$–$C_6$alkyl, or $C_1$–$C_6$alkoxy-$C_1$–$C_6$alkyloxy, and $R_3$ is $C_1$–$C_6$alkyl comprising (a) the reaction of a compound of formula II

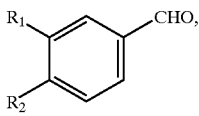                                   (II)

wherein $R_1$ and $R_2$ are as defined hereinbefore, with a compound of formula III,

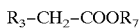                                   (III), wherein $R_3$ is as defined hereinbefore, to form a compound of formula IV,

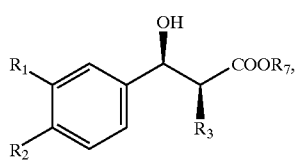                                    (IV)

wherein $R_7$ is $C_1C_{12}$alkyl, $C_3$–$C_8$cycloalkyl, phenyl or benzyl, (b) the isolation of the crystalline compound of formula IV, the conversion of the OH group to a leaving group, and the reaction of a compound containing a leaving group in the presence of a strong base to form a compound of formula V,

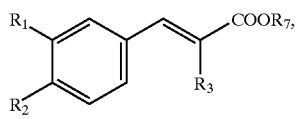                                    (V)

(c) the hydrolysis of the carbonic esters of formula V to form the carboxylic acid of formula VI,

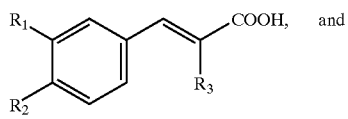                                   (VI)

(d) the hydrogenation of the carboxylic acid of formula VI in the presence of hydrogen and catalytic quantities of a metal complex as asymmetric hydrogenation catalyst, comprising metals from the group of ruthenium, rhodium and iridium, to which the chiral bidentate ligands are bonded, to form a compound of formula I.

2. A process according to claim 1, comprising $R_1$ as methoxy-$C_1$–$C_4$alkyloxy or ethoxy-$C_1$–$C_4$alkyloxy and $R_2$ as methoxy or ethoxy.

3. A process according to claim 2, comprising $R_1$ as 1-methoxyprop-3-yloxy and $R_2$ as methoxy.

4. A process according to claim 1, comprising $R_3$ as a linear or branched $C_1$–$C_4$alkyl.

5. A process according to claim 4, comprising $R_3$ as isopropyl.

6. A process according to claim 1, comprising $R_1$ as 1-methoxy-n-propyloxy, $R_2$ as methoxy, and $R_3$ as isopropyl.

7. A process according to claim 1, comprising the processing of step a) at low temperatures in the presence of a secondary lithium amide.

8. A process according to claim 1, comprising in step b) first acylation of the hydroxyl group and then elimination at low temperatures in the presence of an alkali metal alcoholate in the reaction mixture of the acylation process.

9. A process according to claim 1, comprising step c) being carried out in the reaction mixture of step b).

10. A process according to claim 1, comprising step d) being carried out in the presence of metal complexes of formula VII or VIIa as hydrogenation catalysts,

                                  (VII),

                                  (VIIa), wherein

Me is rhodium;

Y stands for two olefins or one diene;

Z is Cl, Br or I;

$E^-$ is the anion of an oxygen acid or a complex acid; and

L is a chiral ligand from the ditertiary diphosphine group, in which the phosphine groups are are bonded to a $C_2$–$C_4$ chain of the diphosphine backbone chain, and the diphosphine forms a five to seven-member ring together with the rhodium atom.

11. A process according to claim 10, comprising L as formula VIII or VIIIa,

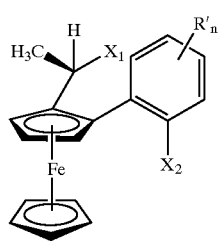                                   (VIII)

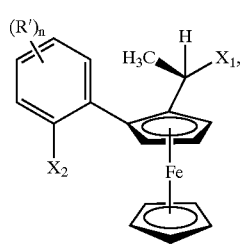                                   (VIIIa)

wherein n is 0 or an integer from 1 to 4 and R' represents the same or different substituents from the $C_1$–$C_4$alkyl, —$CF_3$ and $C_1$–$C_4$alkoxy group; and $X_1$ and $X_2$ are, independently of one another, secondary phosphino.

12. A process according to claim 11, comprising the $X_1$ and $X_2$ groups being the same or different and corresponding to formula —$PR_8R_9$, wherein $R_8$ and $R_9$ are the same or different and are branched $C_3$–$C_8$alkyl, $C_3$–$C_8$cycloalkyl, or unsubstituted phenyl or phenyl substituted with one to three $C_1$–$C_4$alkyl, $C_1$–$C_4$alkoxy, or —$CF_3$.

13. A process according to claim 11, comprising in formulae VIII and VIIIa n as 0, and $X_1$ and $X_2$ as a $PR_8R_9$ group, wherein $R_8$ and $R_9$ are in each case cyclohexyl, phenyl or phenyl substituted with 1 or 2 methyl, methoxy or $CF_3$.

14. A process according to claim 1, comprising step d) being carried out at temperatures of −20 to 150° C.

15. A process according to claim 1, comprising step d) being carried out under positive pressure.

16. A process according to claim 1, comprising pressure conditions at $10^5$ to $2\times10^7$ Pa (Pascal).

17. Compounds of formula IX,

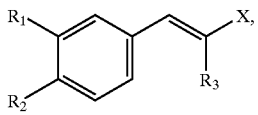

(IX)

wherein $R_1$ and $R_2$ independently of one another, are $C_1$–$C_6$alkyl, $C_1$–$C_6$halogenalkyl, $C_1$–$C_6$alkoxy, $C_1$–$C_6$alkoxy-$C_1$–$C_6$alkyl, or $C_1C_6$alkoxy-$C_1$–$C_6$alkyloxy, $R_3$ is $C_1$–$C_6$alkyl, and X is the -COOH group.

18. Compounds according to claim 17, comprising $R_1$ as methoxy-$C_1$–$C_4$alkyloxy or ethoxy-$C_1$–$C_4$alkyloxy and $R_2$ as methoxy or ethoxy, $R_3$ as $C_1$–$C_4$alkyl, and X as the —COOH group.

19. Compounds according to claim 18, comprising $R_1$ as 1-methoxy-n-propyloxy and $R_2$ as methoxy, $R_3$ as isopropyl, and X as the —COOH group.

* * * * *